(12) United States Patent
Huang et al.

(10) Patent No.: US 12,012,369 B2
(45) Date of Patent: Jun. 18, 2024

(54) ANTIMICROBIAL PHENOLIC FATTY ACID-BASED EPOXY CURING AGENTS FOR EPOXIES

(71) Applicant: The United States of America, as represented by the Secretary of Agriculture, Washington, DC (US)

(72) Inventors: Kun Huang, Conshohocken, PA (US); Richard D. Ashby, Glenside, PA (US); Xuetong Fan, North Wales, PA (US); Helen N. Lew, Wynnewood, PA (US); Robert A. Moreau, Quakertown, PA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 765 days.

(21) Appl. No.: 16/999,142

(22) Filed: Aug. 21, 2020

(65) Prior Publication Data
US 2021/0094905 A1 Apr. 1, 2021

Related U.S. Application Data

(60) Provisional application No. 62/906,768, filed on Sep. 27, 2019.

(51) Int. Cl.
| | | |
|---|---|---|
| C07C 231/02 | (2006.01) | |
| A01N 43/50 | (2006.01) | |
| C07D 233/08 | (2006.01) | |
| C08G 59/52 | (2006.01) | |
| C07C 237/10 | (2006.01) | |

(52) U.S. Cl.
CPC ............ *C07C 231/02* (2013.01); *A01N 43/50* (2013.01); *C07D 233/08* (2013.01); *C08G 59/52* (2013.01); *C07C 237/10* (2013.01)

(58) Field of Classification Search
CPC .. C07C 231/02; C07C 237/02; C08G 59/5046
See application file for complete search history.

(56) References Cited

PUBLICATIONS

Huang, Phenolic fatty acid-based epoxy curing agent for antimicrobial epoxy polymers, Progress in Organic Coatings, 141, Jan. 2020 (Year: 2020).*

* cited by examiner

*Primary Examiner* — Johann R Richter
*Assistant Examiner* — Danielle Johnson
(74) *Attorney, Agent, or Firm* — John Fado; John Henri

(57) ABSTRACT

Compositions containing at least one compound of formula I

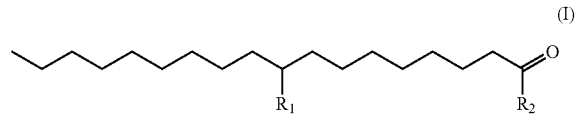

where R1 is a phenolic compound (e.g., simple phenol, creosote, thymol, or carvacrol), and where R2 is a polyamine (e.g., ethylenediamine (EDA), diethylenetriamine (DETA), triethylenetetramine (TETA), tetraethylenepentamine (TEPA), hexamethylenediamine (HDA)); and optionally a carrier; the compositions may additionally contain at least one epoxy resin. Methods for killing microorganisms involving contacting the microorganisms with an effective microorganism killing amount of the above composition. Compositions containing at least one compound produced by a method involving reacting phenolic-branched chain fatty acid methyl ester with at least one polyamine.

10 Claims, 12 Drawing Sheets

ANTIMICROBIAL PHENOLIC FATTY ACID-BASED EPOXY CURING AGENTS FOR EPOXIES

REFERENCE TO RELATED APPLICATION

This application claims the benefit of U.S. Provisional Application No. 62/906,768, filed 27 Sep. 2019, which is incorporated herein by reference in its entirety.

BACKGROUND OF THE INVENTION

Disclosed herein are compositions containing at least one compound of formula I

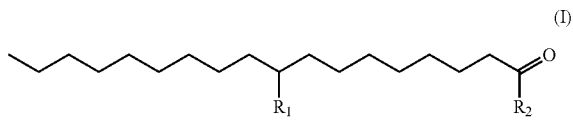

(I)

where R1 is a phenolic compound (e.g., simple phenol, creosote, thymol, or carvacrol), and where R2 is a polyamine (e.g., ethylenediamine (EDA), diethylenetriamine (DETA), triethylenetetramine (TETA), tetraethylenepentamine (TEPA), hexamethylenediamine (HDA)); and optionally a carrier; the compositions may additionally contain at least one epoxy resin. Also disclosed are methods for killing microorganisms involving contacting the microorganisms with an effective microorganism-killing amount of the above composition. In addition, compositions containing at least one compound produced by a method involving reacting phenolic-branched chain fatty acid methyl ester (PBC-FA methyl ester) with at least one polyamine.

Antimicrobial agents are very important chemicals for the sterilization of water, as antimicrobial drugs, as food preservatives, and for public sanitization (Kenawy, E. R., et al., J. Polym. Sci. Pol. Chem., 40 (14): 2384-2393 (2002)). However, they can have the limitation of residual toxicity even when suitable amounts of the agent are used (Tan, S. Z., et al., J. Appl. Polym. Sci., 77 (9): 1869-1876 (2000)). Low molecular weight biocides have the disadvantages of also being volatile, chemically unstable, or photolytic. It is apparent that, in principle, the ideal solution to this problem (i.e., microbially contaminated objects or surfaces) is a method for rendering the objects needed to be sterilized resistant to microbial colonization. Antimicrobial polymers can provide a very convenient way for achieving this goal (Kenawy, E. R., et al., Biomacromolecules, 8 (5): 1359-1384 (2007)).

The use of antimicrobial polymers offers promise for minimizing the environmental problems accompanying conventional antimicrobial agents by reducing the residual toxicity of the agents and prolonging the lifetime of the antimicrobial agents. Polymers can be molded into specific shapes. Also, polymeric antimicrobial agents have the advantage that they are nonvolatile, are chemically stable, and do not permeate through skin. Therefore, they can reduce losses associated with volatilization, photolytic decomposition, and migratory issues (Kenawy 2007).

Epoxy resins are one of the most important classes of compounds used in the coating industry. In the epoxy industry, 90% of the commercial epoxy resins are bisphenol A (BPA) type epoxy resins. The epoxy resins are monomers or in some cases oligomers which are useless alone unless they are cured using curing agents. After mixing and curing with curing agents, the epoxy resins can be converted into robust thermosetting polymers of high performance. Since the most commonly used epoxy resins are the same type that is not easy to vary, so it is much more convenient to change the curing agents so that it can provide antimicrobial functionality to the final epoxy polymers. There are so far very few technologies related to the antimicrobial epoxy polymer area. The antifungal character of isophoronediamine cured BPA-based epoxy resins with tethered carbendazim against *Aspergillus fumigatus* and *Penicillium pinophilum* was investigated by Park et al. using an agar diffusion assay, (Park, E. S., et al., J. Appl. Polym. Sci., 80 (5): 728-736 (2001)). Using a slightly different technique, quaternary ammonium salt-functional epoxy compounds were synthesized (U.S. Pat. No. 5,084,096). Coatings were cured with a commercial polyamidoamine hardener (Versamid® 115x70) and cast onto glass slides. These cured polymer films showed strong antimicrobial activity against *Staphylococcus aureus, Streptococcus faecalis, Escherichia coli, Aerobacter aerogenes, Saccharomyces cerevisiae, Cyanophyta oscilaria, Chrysophyta sp., Aspergillus niger*, and *Trichoderma sp*. However, the polymers with quaternary ammonium incorporated are not water resistant due to the hydrophilicity of the ammonium group. Several researchers have used epoxies in conjunction with polydimethylsiloxane copolymers to produce antimicrobial coatings. Pant et al. generated antimicrobial epoxy compounds and subsequently crosslinked them with aminopropyl-terminated polydimethylsiloxane (Pant, R. R., et al., J. Appl. Polym. Sci., 110 (5): 3080-3086 (2008)). In other work, the antimicrobial compound triclosan was tethered to a polysiloxane backbone along with pendant epoxy groups (Thomas, J., et al., Biofouling 2004, 20 (4-5): 227-236 (2004)). Narute et al. used triethylenetetramine to cure epoxidized cottonseed oil but antimicrobial activity was not verified (Narute, P., et al., Progress in Organic Coatings, 88: 316-324 (2015)).

Antimicrobial epoxy polymers are gaining more interest from both academic researchers and industry due to their potential to provide prolonged efficacy with non-volatile and non-migratory properties compared to conventional biocides. Epoxy polymers are also the most convenient and universal raw materials for coating and adhesive products. However, many of these antimicrobial polymers were made or modified from petroleum monomers or polymers (Kugel, A., et al., Progress in Organic Coatings, 72 (3): 222-252 (2011)). There were also other type of polymers containing phosphorus, sulfur, phenol, benzoic acid, and organometallic derivatives (Kenawy, E. R., et al., React. Funct. Polym., 66 (4): 419-429 (2006); Berkovich, A. K., et al., Polym. Sci. Ser. a+, 51 (6): 648-657 (2009); Park, E. S., et al., Int. Biodeter. Biodegr., 47 (4): 209-214 (2001); Carraher, C. E., et al., J. Inorg. Organomet. P, 25 (6): 1414-1424 (2015)). They were all constructed based on petroleum chemicals such as polyethylene backbones which were durable plastics that did not biodegrade in the environment.

Since most bio-based resources are biodegradable, it is therefore necessary to find some bio-based feedstocks to prepare an epoxy curing agent which will hopefully provide antimicrobial activity to the final epoxy polymers. This is also a research gap that needs to be filled.

Recently, we developed a phenolic-branched chain fatty acid (PBC-FA) by arylation of phenol with oleic acid using a modified H+ ferrierite zeolite catalyst (FIG. 1)(Fan, X., et al., J. Food Prot., 80 (1): 6-14 (2017); Ngo, H. L., et al., European J. of Lipid Sci. and Tech., 116 (3): 344-351 (2014); Yan, Z., et al., Industrial Crops and Products, 114:

115-122 (2018)). Then, the bioactivity of the PBC-FA mixture for their antimicrobial properties against both gram-positive and gram-negative bacteria were evaluated. Results showed that PBC-FAs were a potent antimicrobial against gram-positive bacteria. We theorized that if we can convert PBC-FA into polymers then it might be possible to get both antimicrobial and environmentally friendly bio-based polymer materials to overcome the low molecular weight biocides' defects as well as the defects of prior antimicrobial epoxy polymers.

Herein we report the preparation of antimicrobial PBC-FA-based epoxy curing agents for epoxy coatings. The epoxy curing agent was synthesized from the amidation of PBC-FA with a polyamine (e.g., EDA). For comparison, stearic acid (SA) was used as a control since there is no phenolic group on it, and it was converted to a similar amide by reacting with a polyamine (e.g., EDA). We then investigated the relationship between antimicrobial activity and the structures of the commercial epoxy resin cured by these antimicrobial epoxy curing agents.

SUMMARY OF THE INVENTION

Disclosed herein are compositions containing at least one compound of formula I

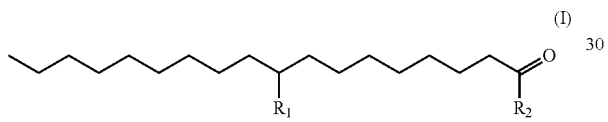

where R1 is a phenolic compound (e.g., simple phenol, creosote, thymol, or carvacrol), and where R2 is a polyamine (e.g., ethylenediamine (EDA), diethylenetriamine (DETA), triethylenetetramine (TETA), tetraethylenepentamine (TEPA), hexamethylenediamine (HDA)); and optionally a carrier; the compositions may additionally contain at least one epoxy resin. Also methods for killing microorganisms involving contacting the microorganisms with an effective microorganism killing amount of the compositions described herein. In addition, compositions containing at least one compound produced by a method involving reacting PBC-FA methyl ester with at least one polyamine.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

Exemplary

Exemplary

Exemplary

Exemplary

Exemplary

Exemplary

Exemplary

Exemplary

Exemplary

Exemplary

Exemplary

DETAILED DESCRIPTION OF THE INVENTION

Figure 1:
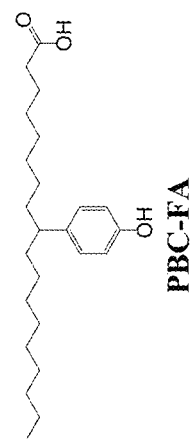
FIG. 1 shows the structure of the phenolic-branched chain fatty acid (PBC-FA as described below).

Disclosed herein are compositions containing at least one compound of formula I

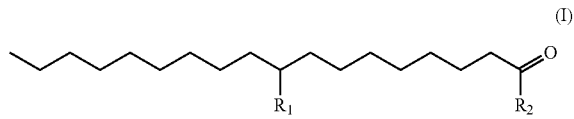

where R1 is a phenolic (e.g., simple phenol, creosote, thymol, or carvacrol), and where R2 is a polyamine (e.g., ethylenediamine (EDA), diethylenetriamine (DETA), triethylenetetramine (TETA), tetraethylenepentamine (TEPA), hexamethylenediamine (HDA)); and optionally a carrier; the compositions may additionally contain at least one epoxy resin. Also methods for killing microorganisms involving contacting the microorganisms with an effective microorganism killing amount of the above composition. In addition, compositions containing at least one compound produced by a method involving reacting PBC-FA methyl ester with at least one polyamine.

Other compounds (e.g., antimicrobials known in the art) may be added to the composition provided they do not substantially interfere with the intended activity and efficacy of the composition; whether or not a compound interferes with activity and/or efficacy can be determined, for example, by the procedures utilized below.

"Optional" or "optionally" means that the subsequently described event or circumstance may or may not occur, and that the description includes instances in which said event or circumstance occurs and instances where it does not. For example, the phrase "optionally comprising a second antimicrobial" means that the composition may or may not contain a second antimicrobial and that this description includes compositions that contain and do not contain a second antimicrobial. Also, by example, the phrase "optionally adding a second antimicrobial" means that the method may or may not involve adding a second antimicrobial and that this description includes methods that involve and do not involve adding a second antimicrobial.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation. Generally the concentration of the compounds will be, but not limited to, about 0.025% to about 10% (e.g., 0.025 to 10%, for example in an aqueous solution), preferably about 0.5% to about 4% (e.g., 0.5 to 4%), more preferably about 1% to about 2% (e.g., 1 to 2%).

The compositions optionally contain a carrier (e.g., agronomically or physiologically or pharmaceutically acceptable carrier). The carrier component can be a liquid or a solid material. The term "carrier" as used herein includes carrier materials such as those described below. As is known in the art, the vehicle or carrier to be used refers to a substrate such as a mineral oil, paraffin, silicon oil, water, membrane, sachets, disks, rope, vials, tubes, septa, resin, hollow fiber, microcapsule, cigarette filter, gel, fiber, natural and/or synthetic polymers, elastomers or the like. All of these substrates have been used for controlled release of effective amounts of a composition containing the compounds disclosed herein in general and are well known in the art. Suitable carriers are well-known in the art and are selected in accordance with the ultimate application of interest. Agronomically acceptable substances include aqueous solutions, glycols, alcohols, ketones, esters, hydrocarbons halogenated hydrocarbons, polyvinyl chloride; in addition, solid carriers such as clays, laminates, cellulosic and rubber matrices and synthetic polymer matrices, or the like.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments and characteristics described herein and/or incorporated herein. In addition, the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions (e.g., reaction time, temperature), percentages and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 10% to a reference quantity, level, value, or amount. For example, about 1.0 g means 0.9 g to 1.1 g and all values within that range, whether specifically stated or not.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Materials: Phenol branched-chain fatty acid (Phenol-BCFA) was prepared according to the method described in our previous publication (Yan, Z., et al., Ind. Crop Prod., 114: 115-122 (2018)). Thymol BCFA (97%), carvacrol BCFA (82.5%) and creosote BCFA (98%) were also prepared according to our method (Yan et al. 2018). Hexamethylenediamine (HDA) (98%), ethylenediamine (EDA) (99%), diethylenetriamine (DETA) (99%), triethylenetetramine (TETA) (mixture of isomers), tetraethylenepentamine (TEPA) (mixture of aliphatic amines) were purchased from Sigma-Aldrich (St. Louis, MO). Phenol (99%) and oleic acid (91.2% C18:1, 6.1% C18:2, 2.7% C18:0), ethylenediamine (99%) and diglycidyl ether of bisphenol A (DGEBA) (M.W.=340.41 g/mol), ethanol and thiazolyl blue tetrazolium bromide were purchased from Sigma-Aldrich (St. Louis, MO). Methyl stearate (99%) was obtained from Fluka Chemika (Buchs, Switzerland). Sulfuric acid (98%) was purchased from J. T. Baker (Center Valley, PA). Tryptic soy agar and broth (TSA and TSB) and were purchased from BD Sciences (Sparks, MD). Peptone (enzymatic digest of protein) was purchased from Becton, Dickinson and Company (Sparks, MD). *E. coli* ATCC700728, *Salmonella Typhimurium* ATCC 53647 and *Listeria innocua* ATCC 33090 were obtained from American Type Culture Collection (Manassas, VA).

Synthesis of PBC-FA: The method has been described in our previous research (Ngo et al. 2014; U.S. Pat. No. 10,071,946). PBC-FA (8.6% methyl-branched chain fatty acids, 3.1% stearic acid, 6.9% lactone, 76.6% pure PBC-FA, 4.2% PBC-FA with two phenols added).

Methylation of PBC-FA to produce PBC-FA methyl ester: 7.4 g PBC-FA, 150 mL methanol and 0.81 g sulfuric acid were added to a 250 mL flask with a magnetic stirrer. The reagents were heated to flux for 2 h. After the reaction removed most of the methanol and ethyl acetate, 50 mL saturated NaHCO$_3$ solution and 50 mL saturated NaCl solution were used to rinse the organic layer 3 times. A rotary evaporator was used to remove the solvent from the organic layer and the sample was placed under vacuum on the rotary evaporator for at least 30 minutes. 7.5 g methyl ester of PBC-FA was obtained. Other type of phenolic branched-chain fatty acid (BC-FA) methyl ester, such as thymol BC-FA, creosote BC-FA, carvacrol BC-FA methyl esters were synthesized in the same way.

Synthesis of PBC-FA-based epoxy curing agent (PBC-FA amide) from PBC-FA and EDA: 3.90 g of PBC-FA methyl ester and 1.80 g of ethylenediamine (EDA) were added into a sealed 20 mL glass vial. The vial was heated to 160° C. for 3 hours. The excess EDA was removed by rotary evaporation at 80° C. for 0.5 h. The crude product PBC-FA amide (PBC-FAA) was a brown viscous liquid. The crude PBC-FAA was purified and separated by flash column chromatography method (methanol/ethyl acetate: 1:4, triethylene amine/methanol: 1:1) to give dimeric PBC-FAA, purified PBC-FAA, mixture of PBC-FAA and PBC-FA imidazoline, and unidentified component. The purified PBC-FAA was a yellowish viscous liquid. Both the crude PBC-FAA and purified PBC-FAA were used as epoxy curing agents for preparing the epoxy films.

Synthesis of stearic acid amide (SAA) from SA and EDA: 4.74 g of methyl stearate and 2.86 g of EDA were combined in a sealed 20 mL vial. The vial was heated to 90° C. for 67 h. After the reaction, 50 mL of ethyl acetate was added into the mixture. The product was not soluble in ethyl acetate, therefore the product precipitated from the solution and then the solution was filtered through filter paper. The product SAA (5.09 g) was obtained as white powder.

Figure 12:
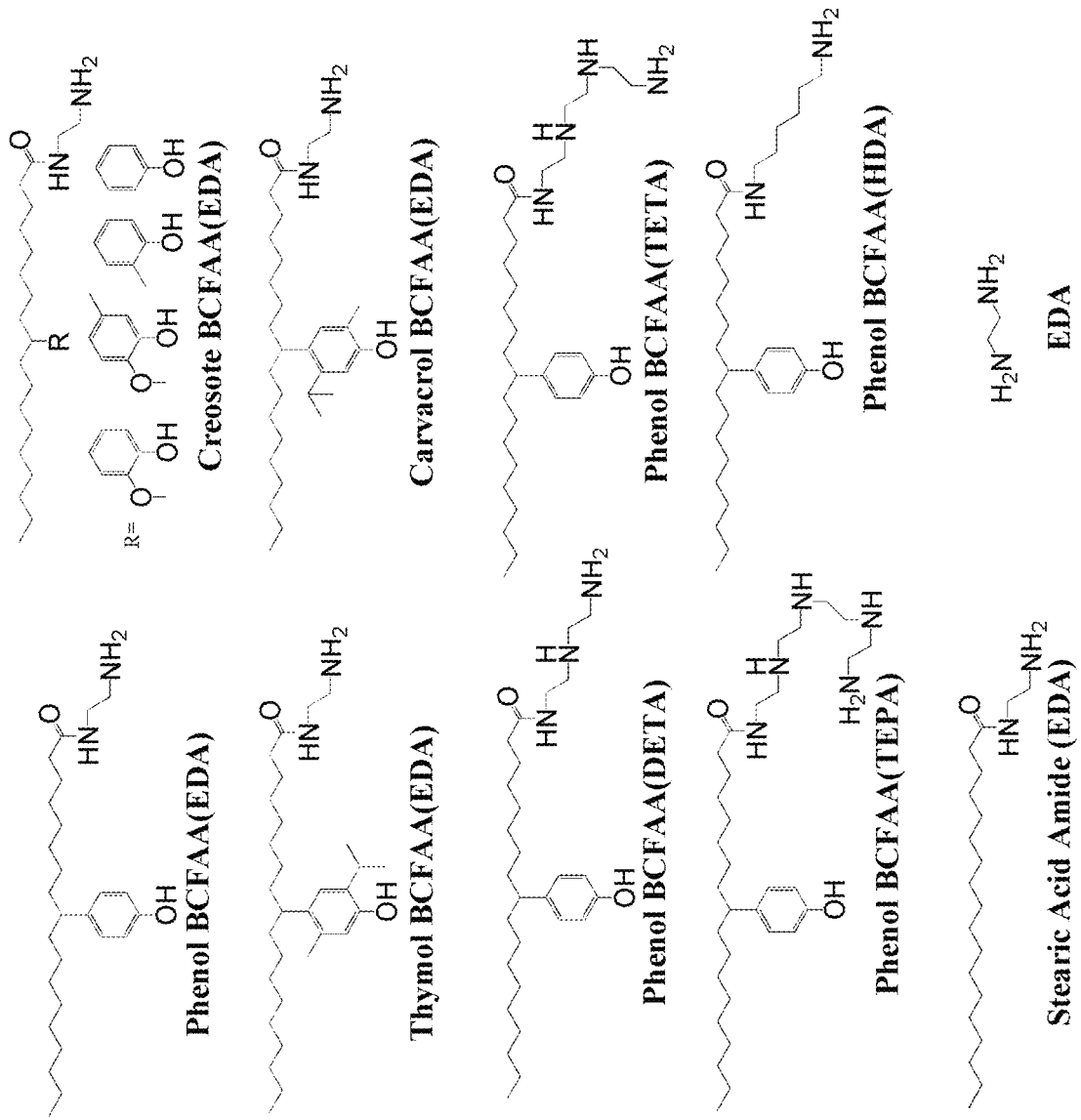
FIG. 12 shows the structures of the curing agents made from different polyamines as described below.

Synthesis of branched chain fatty acid amide (BC-FAA) from phenolic BCFAs and other phenolic compounds: three types of phenolic BCFAs (thymol BCFA, carvacrol BCFA, and creosote BCFA) were converted to phenolic BCFA-methyl esters via methylation. The methyl esters were then converted to phenolic BCFA-amides (phenolic BCFAAs) via amidation. The polyamines including hexamethylenediamine (HDA), diethylenetriamine (DETA), triethylenetetramine (TETA), or tetraethylenepentamine (TEPA) have much higher boiling points than the previously used EDA. One equivalent (100 mol %) of polyamines was used instead of 3 equivalents (300 mol %) which was originally used in the previous work. This was to prevent the need to remove the excess high boiling point amines which can be challenging. The reaction was performed at 160° C. for 3 h, which was the original condition, as well as at 90° C. for 21 h. The agents were further cured with epoxy resin (DGEBA ((diglycidyl ether of bisphenol A))) where 1.00 g of curing agent and DGEBA were blended together in the theoretical stoichiometric weight ratio. The amounts of DGEBA for each epoxy polymer made are listed in Table 2. The structures of curing agents made from different polyamines are shown in FIG. 12.

Preparation of the epoxy polymers: Both the crude and purified PBC-FAAs were individually used as curing agents for a common commercial epoxy resin, diglycidyl ether of bisphenol A (DGEBA). 1.0 g of curing agent and epoxy resin were blended together in the theoretical stoichiometric weight ratio (curing agent:epoxy resin=376 g:340.41 g), 7.0 mL of chloroform was added to dissolve the mixture. The solution was cast either on a Teflon plate for generating the films used in mechanical property tests or on the bottom of a 20 mL glass vial for use in antimicrobial assessment. After air drying at room temperature, the cured films were put into an oven for another 2 h post-curing at 120° C.

Characterization: Gas chromatography (GC) and gas chromatography-mass spectroscopy (GC-MS) GC/FID (Agilent, Model 6890, Hewlett Packard, Model 7890) was used to determine the percent yield of the product in the crude mixture. GC/MS-EI (Agilent, Model GC-7890A and MS-5975CVL-MSD with triple-axis detector) was used to determine the molecular weight of samples using methods that were previously reported (Ngo, H. L., et al., European Journal of Lipid Science and Technology, 116 (3): 344-351 (2014)).

Liquid Chromatography-Mass Spectrometry (LC-MS): Sample LC/MS analysis were performed with a Nano-Acquity ultra performance liquid chromatograph (Waters Co., Milford, MA) equipped with an Acquity UPLC BEH C18, 1.7 µm, (1×100 mm) column (Waters Co.) set at 45° C. and running the following gradient at 80 µL/min: initial time to 2 min water:acetonitrile, 50:50; ramped with a linear gradient to 10 min to water:acetonitrile, 5:95; and returning to the initial conditions at 18 min. with 10 min equilibration time between injections. The solvents contained 0.1% formic acid. The eluent of the column was directed to a quadrupole time of flight mass spectrometer Synapt G1 (Waters Co.) running in positive mode with an electrospray probe in the V mode. Capillary voltage was set to 3 KV, temperature at 350° C., and cone voltage at 40V. The collision energy was set a 6 eV for MS and ramped between 10 and 30 eV for MS/MS.

Fourier-transform infrared spectroscopy (FT-IR): FT-IR was carried out by Bruker Alpha Platinum-ATR. The method followed a conventional attenuated total reflectance (ATR) method (Safar, M., et al., J. Am. Oil Chem. Soc., 71 (4): 371-377 (1994)).

Nuclear magnetic resonance (NMR): All the monomers were analyzed by solution-state proton $^1$H-NMR spectroscopy recorded on 400 MHz Varian NMR spectrometer (Agilent Technologies). All samples were dissolved in deuterated chloroform, with tetramethylsilane (TMS) added for 1H referencing, and their spectra measured at 25° C. The $^1$H spectra had spectral-widths of 9.5 ppm and were acquired with a 45° pulse angle using a 1 s relaxation delay. The gCOSY had a spectral width of 10 ppm in both dimensions and an acquisition time of 0.15 s, using a 1 s relaxation delay. The number of data points in the directly detected dimension was 1200 and 128 increments were collected in indirectly detected dimension with one scan acquired per increment.

Differential scanning calorimetry (DSC): Thermal properties were determined using DSC analysis on a Pyris 1 analytical instrument (Perkin Elmer, Norwalk, CT). The instrument was cooled using a cryogenic cooling system incorporating liquid nitrogen as the coolant. Helium was used as the purge gas at a flow rate of 20 mL/min. The instrument was calibrated using indium (melting temperature (Tm)=156.6° C.) and cyclohexane with transition temperatures of −87° C. and 6° C. Approximately 5 mg of each sample was accurately weighed and placed into sealed sample pans (Kit #0219-0062, Perkin Elmer). The temperature program was as follows: (1) isotherm for 2 min at 25° C., (2) heat from 25° C. to 150° C. at 20° C./min, (3) isotherm for 2 min at 150° C., (4) cool from 150° C. to −50° C. at 100° C./min, 5) isotherm for 2 min at −50° C., 6) heat back from −50° C. to 150° C. at a rate of 20° C./min. Glass transition temperatures (Tg) were taken from the final heating cycle.

Dynamic mechanical analysis (DMA): Dynamic mechanical analysis (DMA) of the samples was performed on a DMA-1 star system (Mettler-Toledo) in tensile mode with a frequency of 1 Hz. The temperature was swept from −20 to 100° C. at 3° C./min. For each sample, two duplicate tests were performed to ensure the reproducibility of data. Tg was determined as the temperature at the maximum of the tan δ versus temperature curve.

Thermogravimetric analysis (TGA): TGA was performed using an SDT Q500 TGA (TA Instruments) instrument. Approximately 10 mg of each sample was accurately weighed and scanned from 25 to 650° C. at a heating rate of 10° C./min under a nitrogen atmosphere.

Antimicrobial test of epoxy films: Freshly cultivated bacterial strains were diluted with 0.1% peptone water to the desired populations. Then 1 mL of the diluted bacteria was added into the glass vials coated with epoxy films on the bottom. These vials were put into the shaking incubator for 24 or 48 h at 37° C. and 100 rpm. After incubation, the bacterial populations were enumerated using a plating method on tryptone soya agar (TSA). For each plate, 100 µL solution was taken out and aseptically plated by an L shape plastic spreader. The colonies on the TSA Petri dishes were counted after incubation at 37° C. for 24 h (*E. coli*) or 48 h (*L. innocua*).

Investigation of possible leaching and reusability of the epoxy polymers: The polymer coatings described above were immersed in 1 mL of 0.1% peptone water and incubated for predetermined times to mimic the test method described above. After 24 or 48 h incubation, the polymer coatings were removed from the peptone water and 10 µL of 4 log CFU/mL bacterial cultures were added into the 1 mL peptone water (final bacterial population: 10$^2$) containing possible leaching chemicals from the coatings. The peptone water containing the bacteria was put back into the shaking incubator for 24 or 48 h (depending on the specific bacterial strain being tested) at 37° C. and 100 rpm. An empty vial without the polymer film was used as a blank control. After incubation, the bacterial populations were enumerated using a plate count method. For each plate, 100 μL samples were removed from the glass vials and aseptically plated with an L shaped plastic spreader on TSA plates. The plates were incubated at 37° C. for 24 or 48 h and the colonies were manually counted.

Minimum Bactericidal Concentration (MBC) and Minimum Inhibitory Concentration (MIC) test of synthesized monomers: The bacterial cultures used in this study were *E. coli* ATCC 700728 and *L. innocua* ATCC 33090. Cultures were obtained from American Type Culture Collection (Manassas, VA). Cultures were grown with 100 rpm agitation in tryptic soy broth (TSB, Difco, Franklin Lakes, NJ, USA) for 18 hours at 37° C.

MBC and MIC of monomers against the two bacterial strains were assessed by the modified 96 well microdilution plate protocol of Magalhaes and Nitschke (Magalhaes, L., and M. Nitschke, Food Control, 29: 138-142 (2013)).

Figure 2:
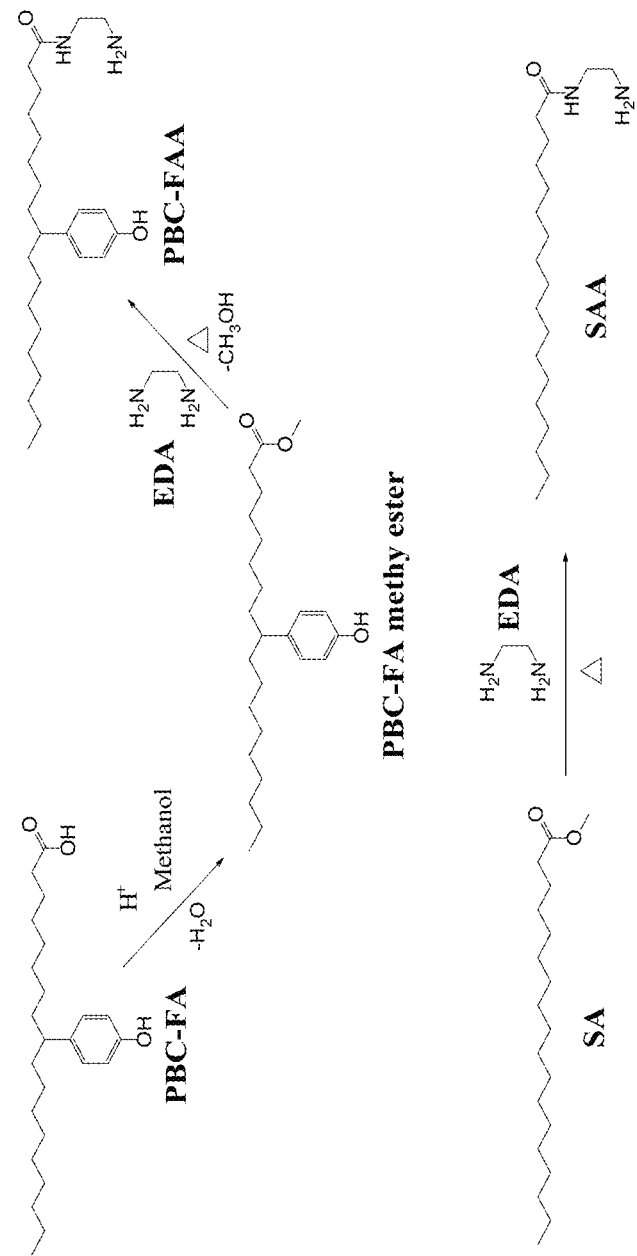
FIG. 2 shows the synthesis of PBC-FA amides (PBC-FAA) as described below.
Figure 3:
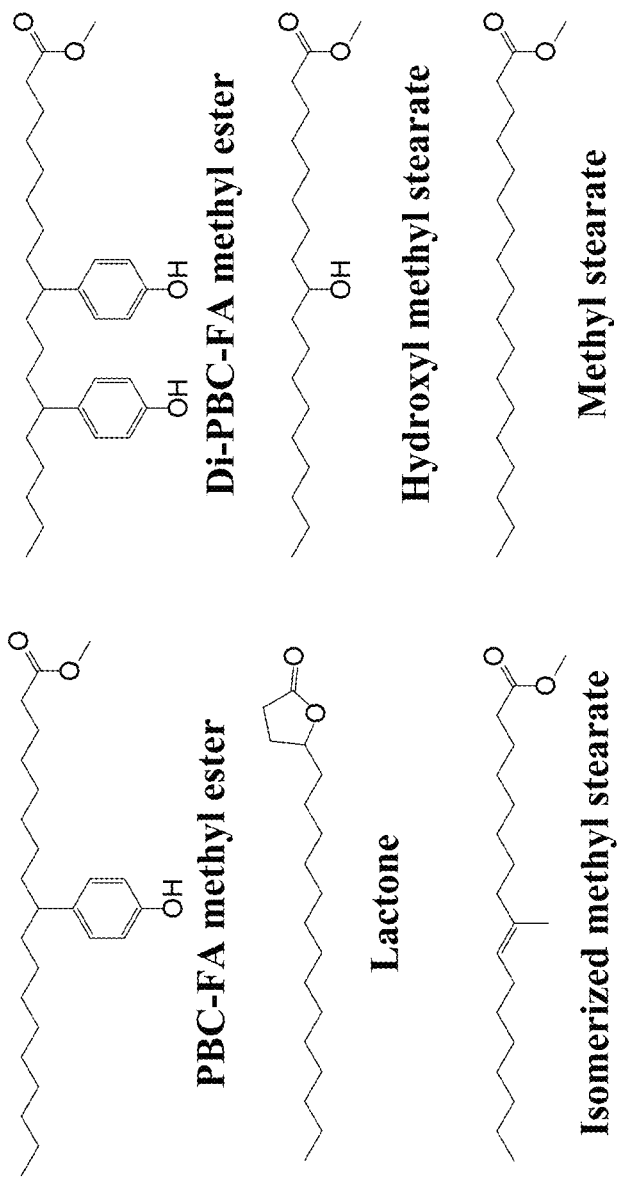
FIG. 3 shows the components from the methylation of PBC-FA as described below.

Results and discussions. Methylation of PBC-FA: PBC-FA is a fatty acid and the direct amidation reaction of fatty acid with amines always needs a high reaction temperature to achieve completion (Huang, K., et al., Polym. J., 42 (1): 51-57 (2010)). To avoid the destruction of PBC-FA by high temperature, it was methylated to form a methyl ester (PBC-FA methyl ester; other alkyls (e.g., C$_{2-4}$) may work but methylation is the cheapest and most efficient way because the methanol is the most volatile alcohol which can promote the amidation reaction in next step). Then PBC-FA methyl ester was reacted with EDA to obtain PBC-FAA (FIG. 2). The GC analysis of the methylation product of PBC-FA showed that it contained 76.6% of PBC-FA methyl ester, 8.59% of isomerized methyl stearate, 3.09% of methyl stearate, 6.91% of lactone with hydroxyl methyl stearate, and 4.81% of other components. According to GC-MS, the PBC-FA with two phenols grafted (di-PBC-FA) methyl esters were found in the 4.81% of other components. FIG. 3 shows the component possibilities in the methylation product of PBC-FA.

Figure 4:
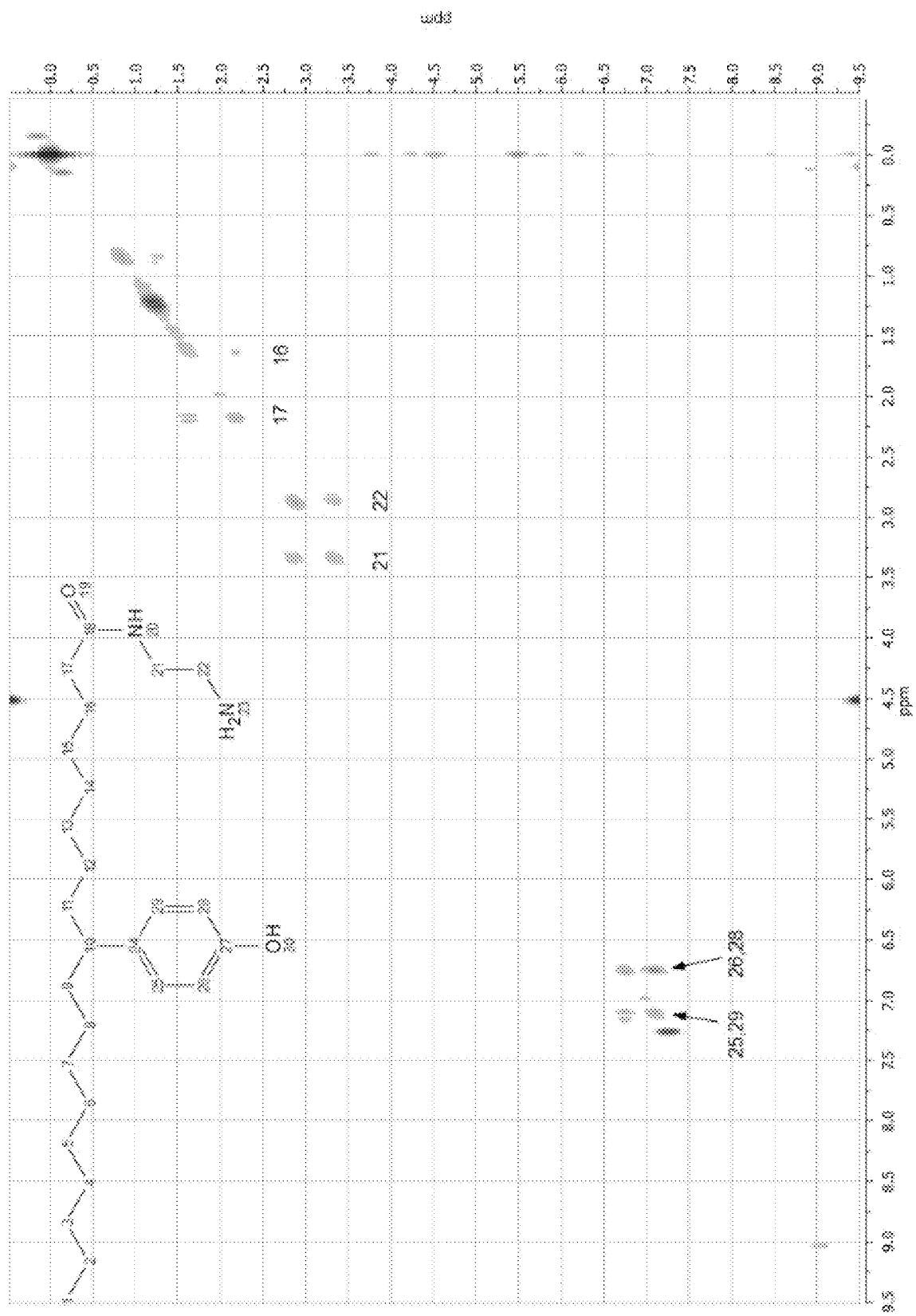
FIG. 4 shows the $^1$H-NMR correlation spectroscopy of purified PBC-FA amides (PBC-FAA) as described below.

Synthesis of PBC-FA-based epoxy curing agent: FIG. 2 shows the amidation reaction from PBC-FA methyl ester to PBC-FAA. We tried to do this reaction at different temperatures ranging from 70°–170° C. The desired product PBC-FAA was separated from a silica gel column and confirmed by two-dimensional $^1$H-NMR correlation spectroscopy (FIG. 4). FIG. 4 displayed correlations between carbon numbers 25-26, 28-29, 21-22, and 16-17 of purified PBC-FAA, which are distributed to aromatic protons, protons between two amino groups, α-carbon protons, and β-carbon protons, respectively.

Figure 5:
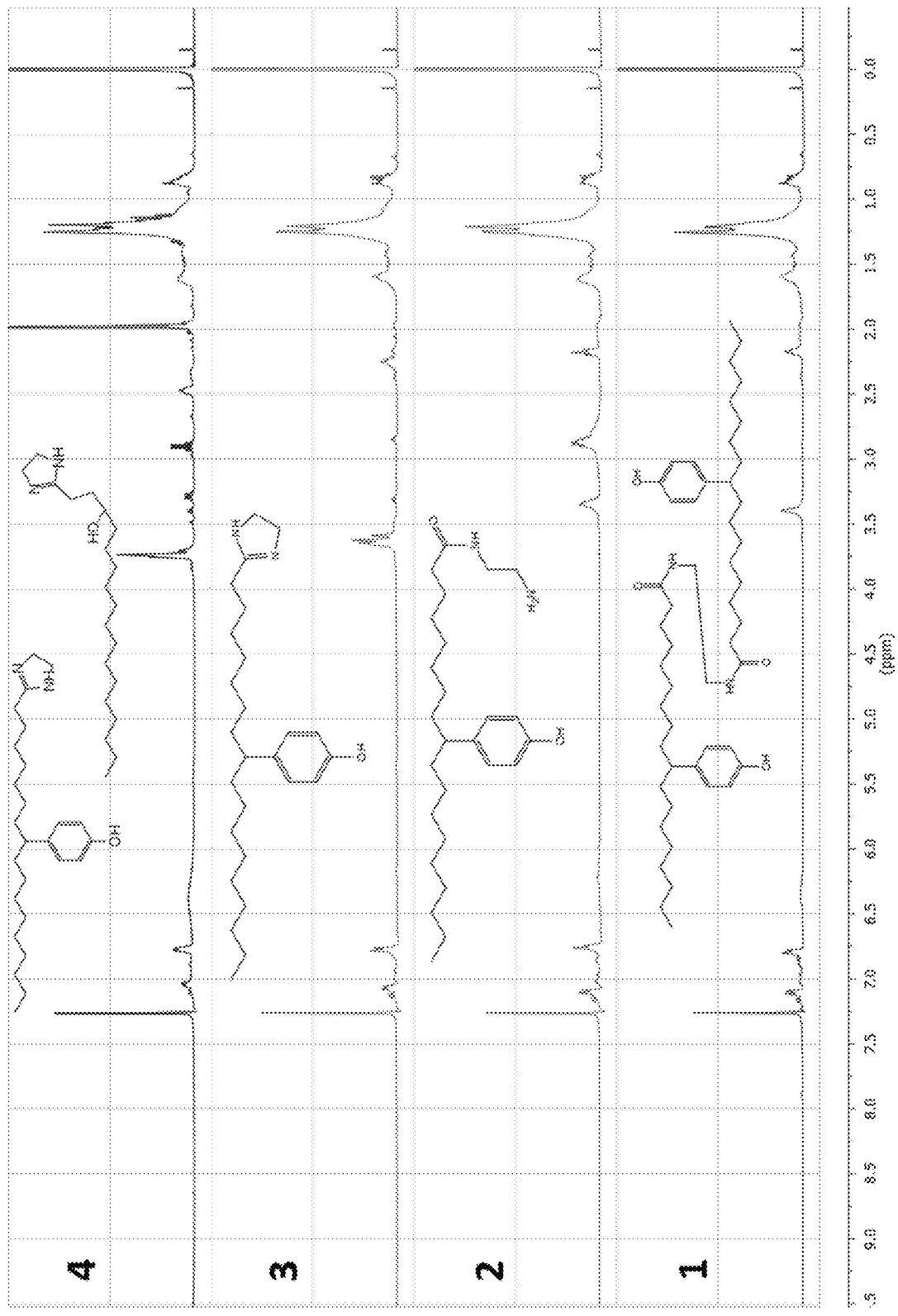
FIG. 5 shows the $^1$H-NMR of compounds in the crude PBC-FAA separated from the silica gel column Exemplary
Figure 6:
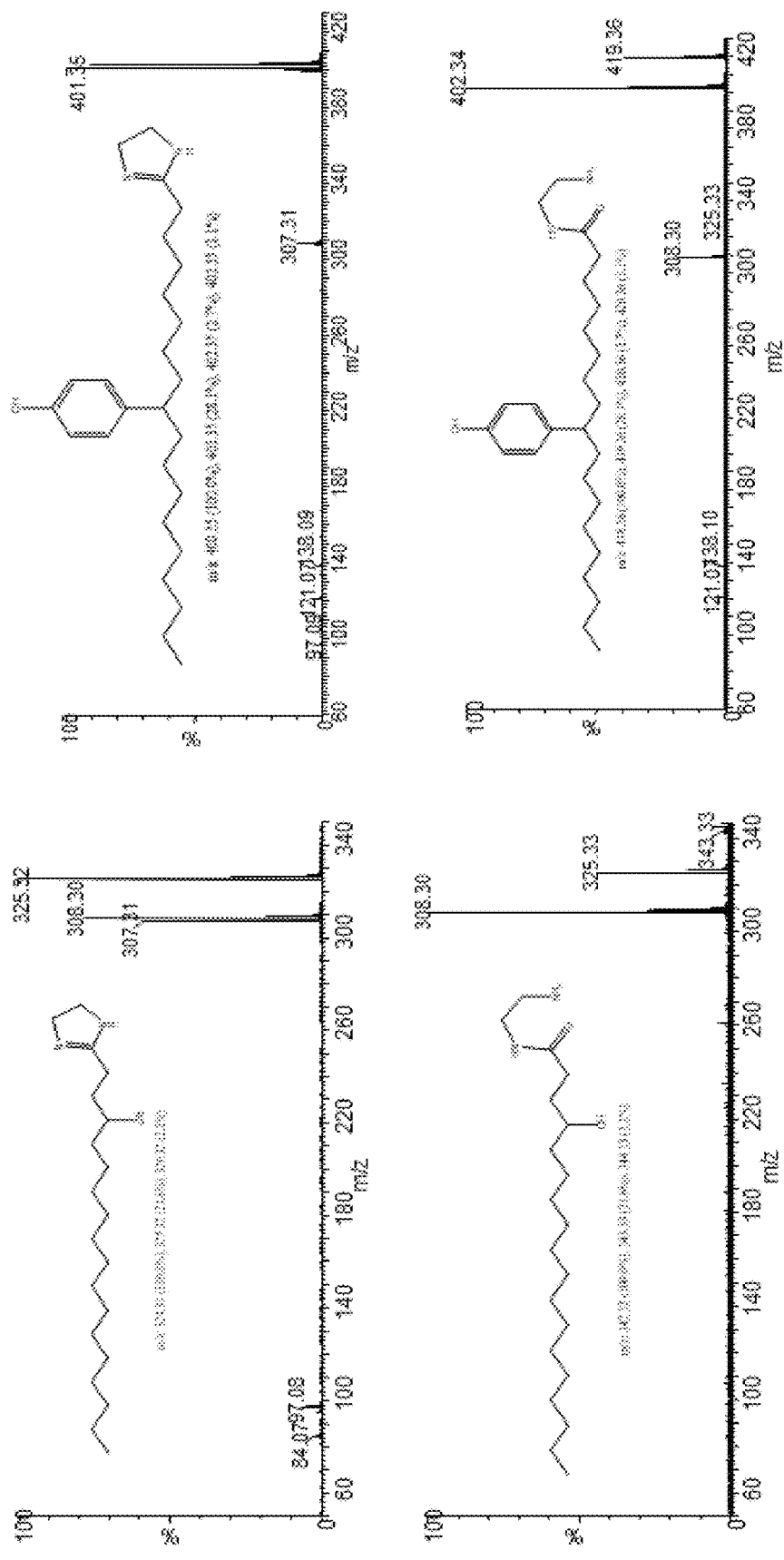
FIG. 6 shows the ion peaks in LC/MS analysis of compound 4 as described below.
Figure 7:
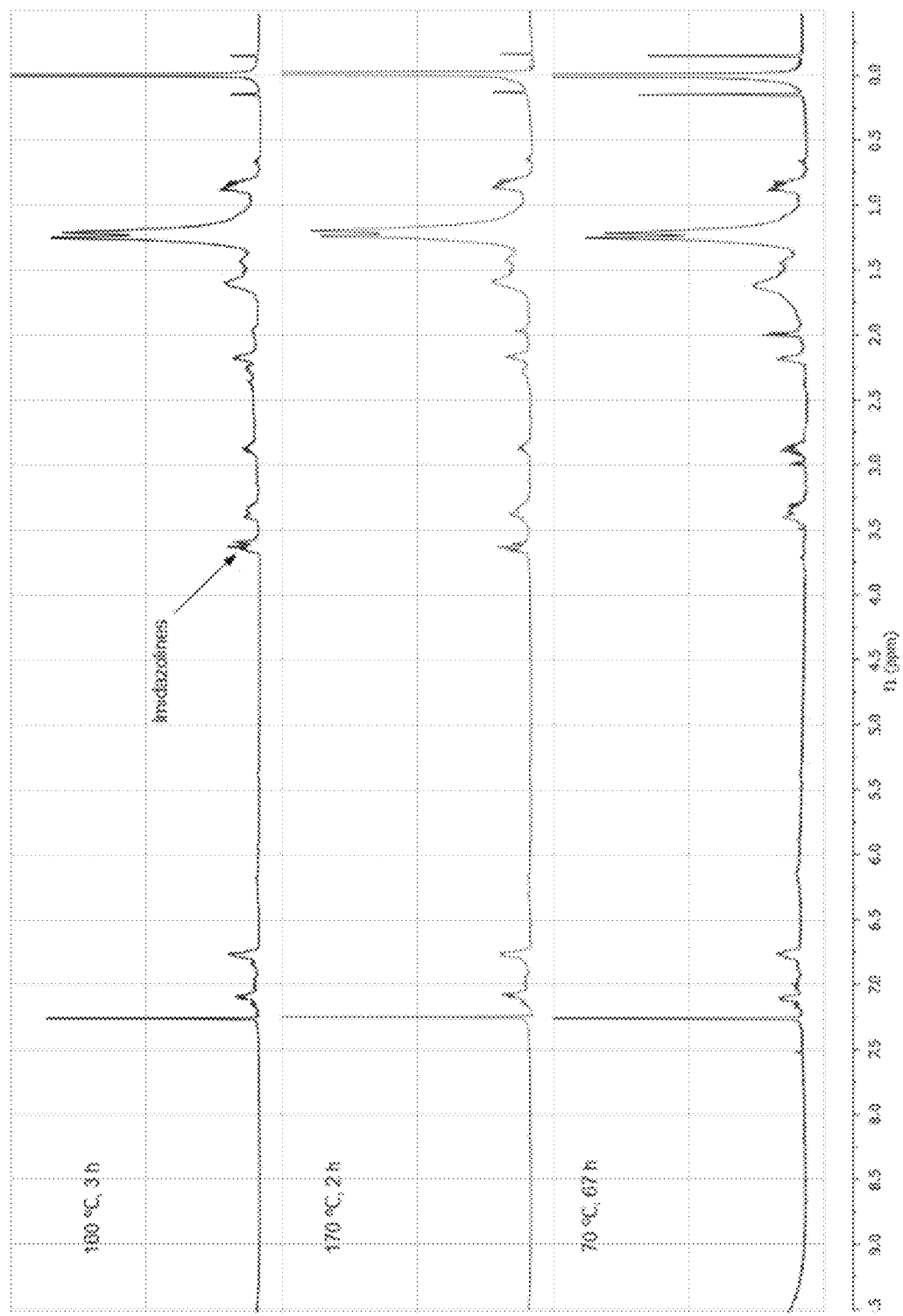
FIG. 7 shows the $^1$H-NMR spectra of crude PBC-FAAs obtained at different reaction conditions as described below.

Based on the $^1$H-NMR of column separated products from crude PBC-FAA (FIG. 5), the major byproducts were dimeric-PBC-FA amides (component 1), imidazolines (component 3), and the water soluble mixture of imidazolines derived from PBC-FA and lactone (component 4), Component 4 has major molecular ion peaks of 325.32 and 401.35 in LC-MS (seen in FIG. 6). Imidazolines were formed by losing water from PBC-FAA at the high reaction temperature. This reaction was attempted at different temperatures ranging from 70°–170° C. If the reaction time was prolonged or the reaction temperature was increased, more imidazolines were generated. FIG. 7 shows the $^1$H-NMR spectra of crude PBC-FAAs obtained at different reaction conditions. It reveals that this reaction almost doesn't form imidazoline at low reaction temperature (70° C.).

Synthesis of stearic acid amide (SA amide) from SA and EDA: As we investigated the antimicrobial activities of the fatty acid derivatives with different structures, the PBC-FAs were found to be very active against Gram-positive bacteria, while the fatty acids without phenolic groups have no activity to these bacteria (Fan et al. 2017). In order to investigate the relationship of activity-structure, a similar amide made from stearic acid without phenolic group was synthesized as well to compare the antimicrobial activity with that of PBCFA amide.

Figure 8:
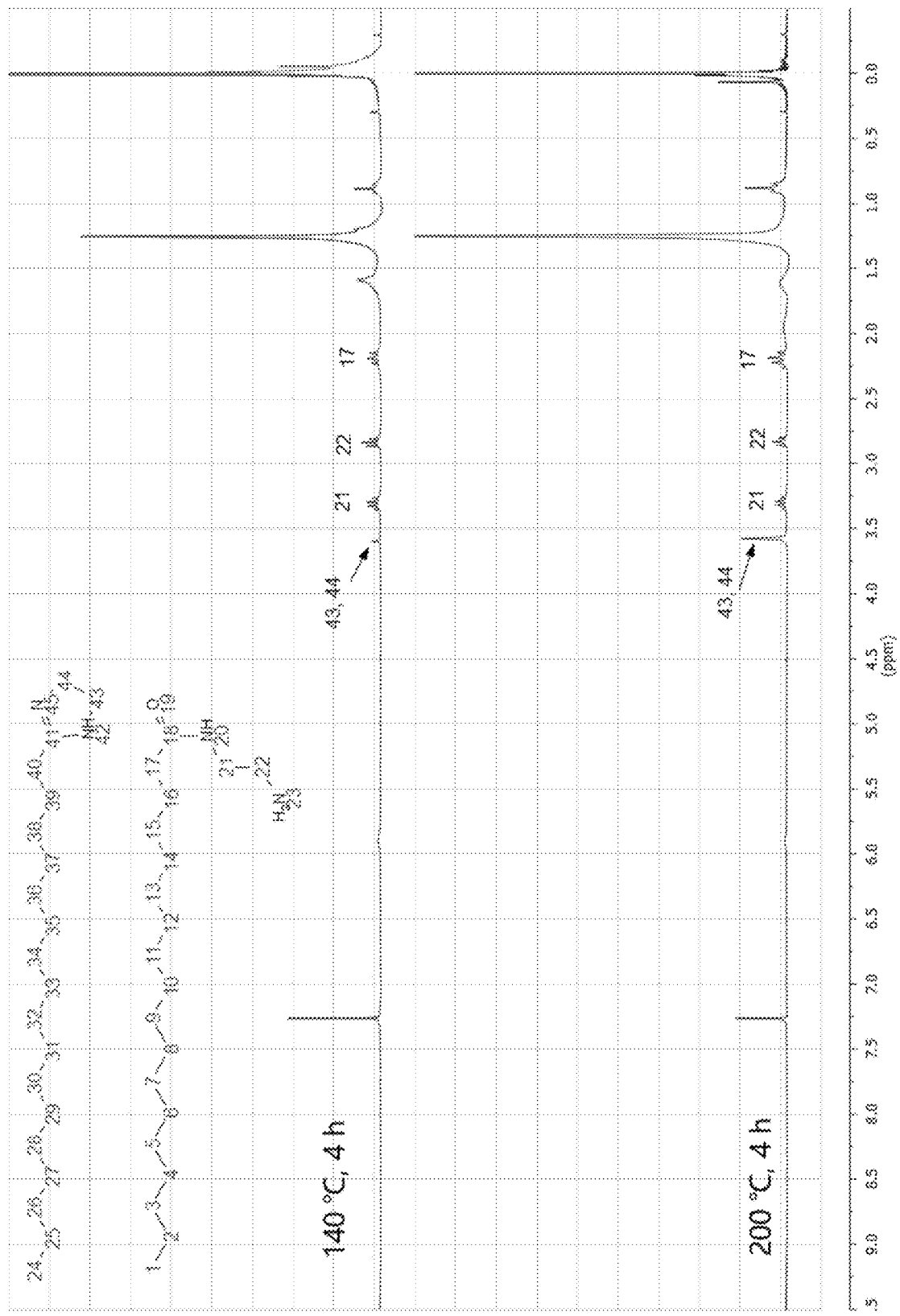
FIG. 8 shows the different imidazoline contents in the product at different temperatures as described below.

The purity of methyl stearate is up to 99%. The main product of amidation was stearic acid amide (SAA), while the side product was stearic imidazoline. The GC-MS results revealed that even when the reaction temperature was set as 90° C., there was still small amounts of imidazoline formed in the product. As shown in FIG. 8, when the reaction temperature increased the content of imidazoline increased. Thus, we tried to carry out this reaction at 90° C. for 70 h to obtain SAA with a relatively lower content of stearic imidazoline.

Figure 9:
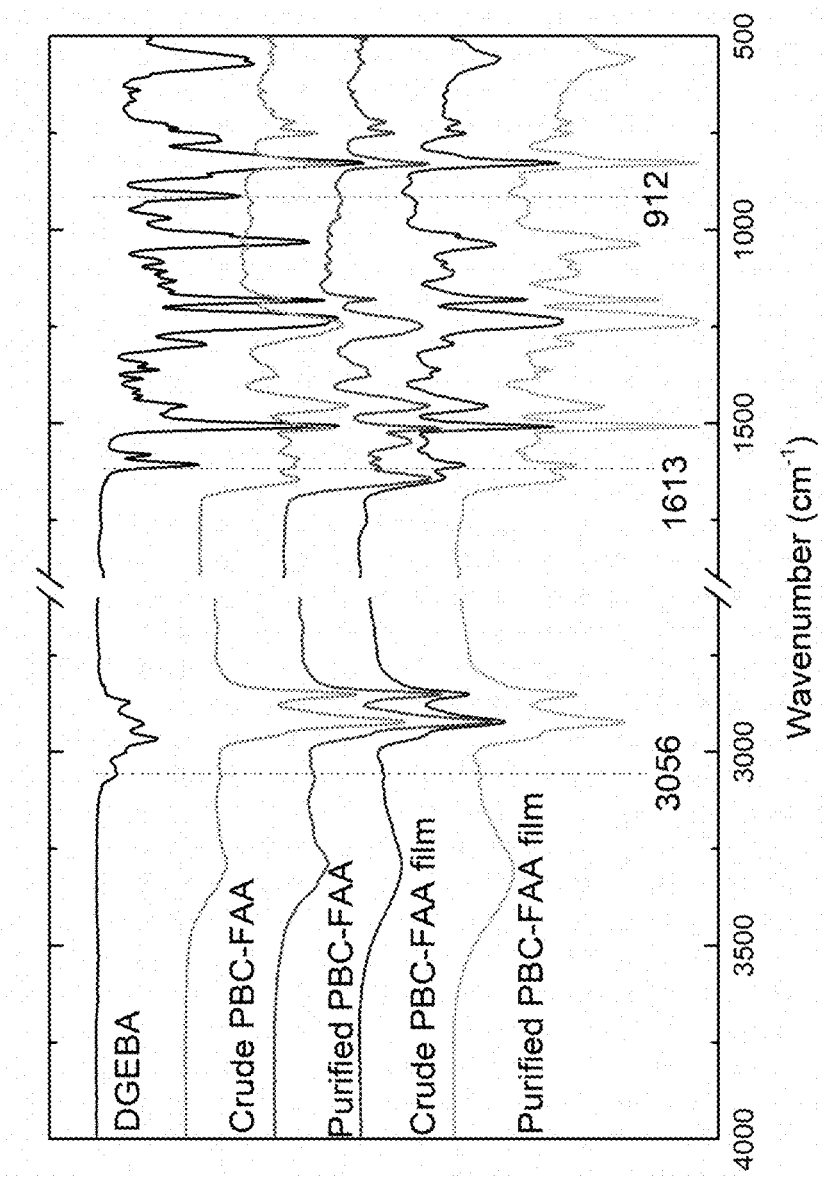
FIG. 9 shows the FT-IR spectra of DGEBA (diglycidyl ether of bisphenol A), crude PBC-FAA, purified PBC-FAA, and the cured epoxy films as described below.

Characterization of epoxy polymer films: The epoxy resin was individually cured by crude and purified PBC-FAAs respectively at the same weight ratio of 376 to 340.41. The crude PBC-FAA contained complicated side products, some of them don't anticipate the curing reaction with epoxy resin. These side products were embedded in the epoxy network. The purified PBC-FAA reacted with DGEBA in a stoichiometric ratio. But the curing reaction is also a complex of epoxy-amine addition reaction and epoxy self-polymerization, both leading the epoxy group to be consumed in the curing process (Peerman, D. E., et al., Ind. Eng. Chem., 49 (7): 1091-1094 (1957)). FIG. 9 is the FT-IR spectra of DGEBA, crude PBC-FAA, purified PBC-FAA, and the epoxy films made from them. There are two typical IR peaks related to the oxirane ring (Cholake, S. T., et al., Defence Science Journal, 64 (3): 314-321 (2014)). The symmetric stretching of C—H (3056 cm$^{-1}$) and C—O stretching of oxirane (912 cm$^{-1}$) can be observed on the DGEBA spectrum, but they disappeared on the spectra of crude PBC-FAA film and purified PBC-FAA film, which indicated that the epoxy group had been opened. The N—H deformation vibration peak at 1613 cm$^{-1}$ also disappeared on the epoxy film spectra (Wang, X. R., et al., J. Appl. Polym. Sci., 43 (12): 2267-2277 (1991)). Thus, it was concluded that the primary amine of PBC-FAA attacked the epoxy ring, resulting in the opening of the epoxy rings. As the epoxy rings were all opened, it was confirmed that the epoxy films gained complete curing.

Figure 10:
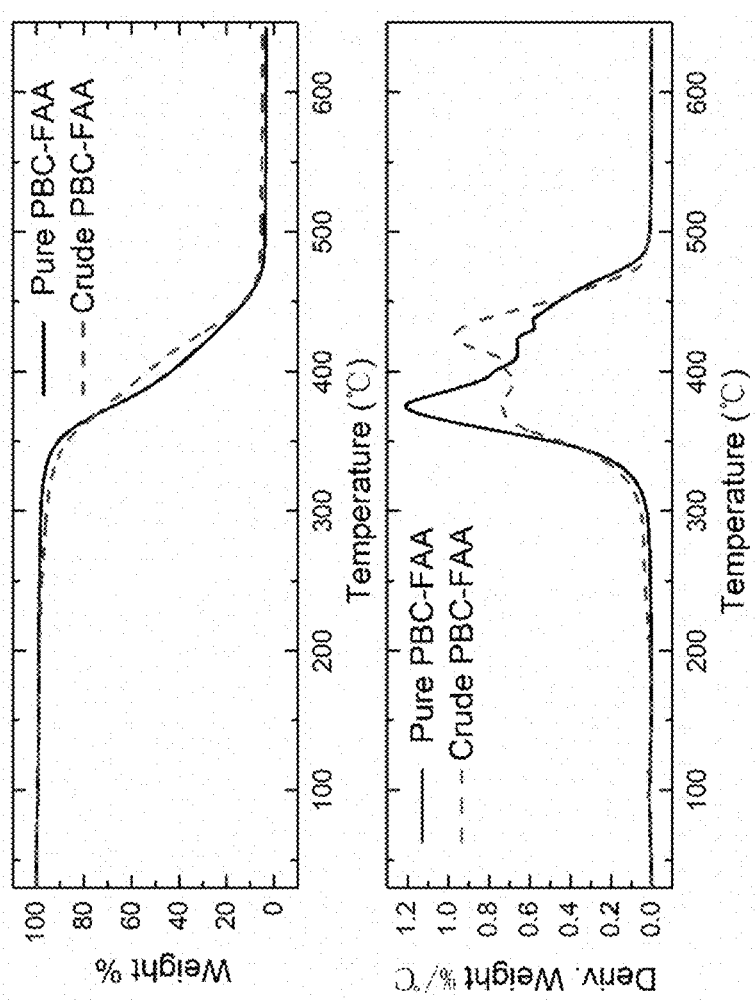
FIG. 10 shows the TGA (Thermogravimetric analysis) of cured epoxy films made from DGEBA cured by purified and crude PBC-FAA as described below.
Figure 11:
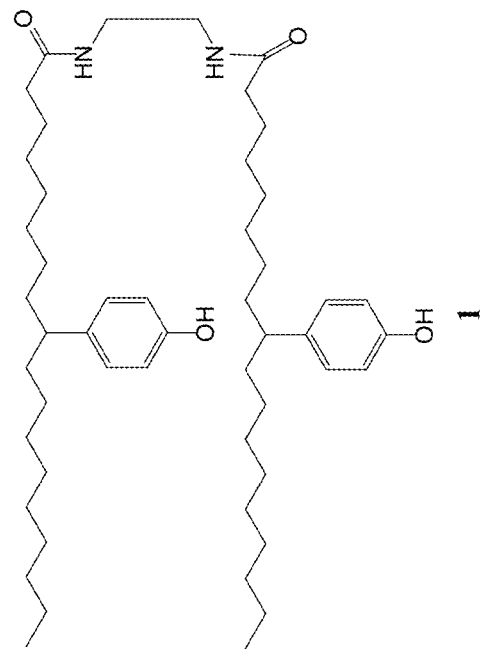
FIG. 11 shows compounds 1-3 as described below.
Figure 11:
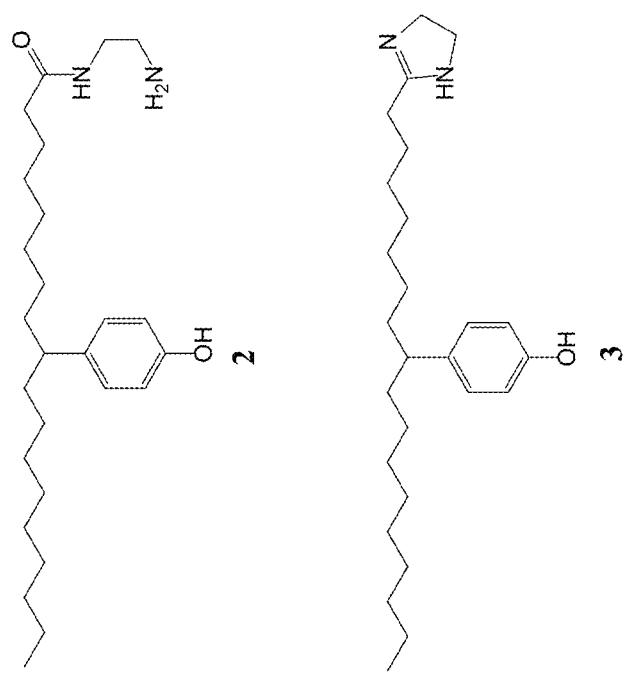

Mechanical and thermal properties of epoxy polymer films: The crude PBC-FAA contained di-PBC-FAA, purified PBC-FAA, imidazolines, and other unknown compounds. Only the compounds having primary or secondary amino groups can crosslink with epoxy resin so that they can form an epoxy network. Di-PBC-FAA has no reactive amino group, thus it can only be a filler compound embedded in the network. Imidazolines could be a latent curing agent for epoxy resin at high temperature, but they can only be a catalyst but not a cross-linker (U.S. Pat. No. 4,335,228 (1982)). None of these compounds were reactive to epoxy resin and were still existing in the cured epoxy network as small molecules or oligomers. The TGA of cured epoxy films made from DGEBA cured by purified and crude PBC-FAA is displayed in FIG. 10. Derivative of weight loss of crude PBC-FAA indicated a two-stage weight loss, attributing to low molecular weight compounds and epoxy polymers, respectively. Regarding the purified PBC-FAA, there was basically only one weight loss peak in the derivative weight graph, which means the epoxy films cured by purified PBC-FAA gained much more complete curing, and thus contained much less free monomer than that cured by crude PBC-FAA.

Antimicrobial activity of the polymer films: The epoxy films were cast on the bottom of glass vials. 0.1% peptone water was used as a medium to prepare the bacterial solution. Since peptone water is nutritious to the growth of bacteria, this test approach actually measured the inhibition ability of the polymer films to the bacteria. The antimicrobial test result of the epoxies (Table 1) shows the effectiveness of epoxy films cured by different curing agents. The structure of purified PBC-FAA, SAA, and EDA are shown in FIG. 2. Surprisingly, the epoxy film cured by purified PBC-FAA significantly inhibited the growth of Gram-positive bacteria L. innocua 33090, while the crude PBC-FAA cured epoxy film surprisingly inhibited the growth of both the Gram-positive L. innocua 33090 and Gram-negative E. coli 700728. However, the SAA cured epoxy film showed no obvious inhibition to L. innocua (L. innocua) or E. coli. EDA was used as another control to cure the epoxy film and the film showed slight inhibition towards L. innocua but almost no effect on E. coli.

The results indicated that the phenolic group on the fatty acid chain was of great importance for the inactivation of bacteria. SAA has no phenolic group, and compared to the purified PBC-FAA, SAA cured films, had no obvious effect on the bacteria. EDA has no amide, phenol, or fatty acid chain moieties, so it had less antimicrobial activity than purified PBC-FAA but was more active than SAA in the case of Gram-positive Listeria innocua 33090. Crude PBC-FAA is a very complicated mixture of the purified PBC-FAA and other side products. In spite of the inactivity of purified PBC-FAA itself towards E. coli, the crude PBC-FAA surprisingly had strong antimicrobial activity against E. coli, indicating that there are some other side products present in crude PBC-FAA that inactivated E. coli.

Many different amides such as thymol BC-FAA, creosote BC-FAA, and carvacrol BC-FAA were made at two different temperatures, but only a few of them demonstrated antimicrobial activity (Table 3). Both EDA and stearic acid amide (EDA) as curing agents were not active against bacteria and would not be considered as antimicrobial epoxy polymers. Therefore, the phenol moiety must surprisingly play a key role in imparting antibacterial qualities to the fatty acid chain. As the phenol is the key, we suspected that other phenolic compounds, especially other natural phenolic compounds, can also perform equally well. Thymol, carvacrol and creosote BC-FAs were converted to BC-FAAs using the same method and were then used to cure the epoxy resin, DGEBA. We surprisingly found that only creosote BC-FAA was an antibacterial epoxy curing agent for the polymer (Table 3). Creosote contains about 7% phenol, while the other two major components, guaiacol, cresol and 4-methylguaiacol comprise about 70% of creosote. To exclude the influence of phenol, 7% of phenol-BC-FAA was added into thymol BC-FAA to mimic the creosote BC-FAA. However, the epoxy polymer derived from thymol BC-FAA with 7% of phenol-BC-FAA surprisingly did not inhibit the growth of E. coli. This meant that the other major components in the creosote (guaiacol, cresol and 4-methylguaiacol) were involved to enable the polymer to inhibit the bacteria.

For synthesis of amide curing agents, we tried different reaction temperatures. High temperatures will increase the possibility of side reactions and by-products. Firstly, the amidation reaction was conducted at 90° C. for 21 h. Low temperature and long reaction time could ensure that less side reactions occur. Phenol-BC-FAA (EDA, 90° C.) and creosote BC-FAA (EDA, 90° C.) were antibacterial against only L. innocua (Gram-positive). Surprisingly, when these two polymers were made at 160° C. for 3 h, the epoxy polymers that were cured by them could inhibit L. innocua (Gram-positive), E. coli (Gram-negative), and Salmonella (Salmonella Typhimurium, Gram-negative). Thymol BC-FAA (EDA) prepared at both 90° C. and 210° C. to conduct the same test, were surprisingly both inactive against any bacteria. We can learn from these results that the temperature of the amidation reaction is an important factor to enable the curing agent to have Gram-negative inactivation capability.

Different types of amines with different active hydrogen densities such as ethylenediamine (EDA), hexamethylenediamine (HDA), diethylenetriamine (DETA), triethylenetetramine (TETA) and tetraethylenepentamine (TEPA) were used to prepare various curing agents by reacting with phenol-BC-FA. The antimicrobial test results are shown in Table 4. HDA has two primary amino groups, the same as EDA, but a longer aliphatic chain than EDA. Because of this, phenol-BC-FAA (HDA) has little to no activity against bacteria. Without being bound by theory, seems that the antibacterial activity is related to the hydrophilic-lipophilic balance of the polymer. Because HDA is more lipophilic than EDA, phenol-BC-FAA (HDA) made at 160° C.) lost antibacterial activity. Other amines like DETA, TETA and TEPA were also tested, but they have more than two amino groups, so the formulas need more epoxy resin which makes these final polymers too lipophilic. Even though phenol BC-FAA (EDA) shows good inhibition against both Gram-positive and Gram-negative bacteria, phenol-BC-FAA (DETA), phenol-BC-FAA (TETA) and phenol-BC-FAA (TEPA) surprisingly did not show any activity against bacteria. This result is similar to the EDA and stearic acid amide cured epoxy polymers. EDA has a small molecular weight, thus 1 mol EDA requires 2 mol epoxy resin to fully crosslink. Stearic acid amide (SAA) is more lipophilic than phenol-BC-FAA (EDA), but it also increased the lipophilicity of the resulted epoxy polymer. Based on these data, we can conclude that the lipophilicity surprisingly has an adverse effect on the antibacterial activity of the polymer.

Without being bound by theory, there could be several reasons for polymer coatings being antimicrobial, but there is also a possibility that polymers contain impurities such as antimicrobial small molecules. These small molecules leach out of the polymer matrix into the medium for antimicrobial tests and contribute to the antimicrobial activity. To this end, Phenol-BC-FAA films made at 160° C. were immersed in peptone water and incubated for 24 h. The films were removed from the water and the residual peptone water was tested to evaluate any possible small molecules that had leached out from the polymers. The peptone water was then used as a media to incubate bacteria ($10^2$ population) for another 24 h. The test result showed that the peptone water incubated with a Phenol-BC-FAA (EDA) film did not inhibit the growth of E. coli, which indicated that the Phenol-BC-FAA (EDA) film made at 160° C. was inherently antibacterial, and that the antimicrobial capability was not attributed to small molecules leaching out of the polymer.

Since bacterial inhibition was not associated with small molecules leaching from the polymer but was attributed to the structure of the polymer, reusability tests were carried out by reusing Phenol 97% BC-FAA (EDA, 160° C.) in succession for 3 tests. Each test was composed of three replicates (Table 5). The second reuse showed that both Phenol 97% BC-FAA (EDA, 160° C.) and Phenol 72% BC-FAA (EDA, 160° C.) surprisingly maintained good inhibition activity (seen in Table 5). The third reuse showed that the antibacterial capability of one replicate amid both Phenol 97% BC-FAA (EDA, 160° C.) and Phenol 72% BC-FAA (EDA, 160° C.) had weakened. This result shows that the antibacterial polymer is surprisingly reusable, but its function will attenuate as the number of repeated uses increases.

Antimicrobial activity of the monomers: We tried to separate these active side products from crude PBC-FAA. The compounds separated from the silica gel column shown in FIG. 5. To evaluate the antimicrobial activity of these fractions, the MIC and MBC of these fractions have been tested. If we can figure out the antimicrobial monomers against E. coli then we can understand why the crude PBC-FAA was also inhibitory towards E. coli. The MIC and MBC results are exhibited in Table 6. Compound 1 is the di-PBC-FAA with two PBC-FA chain, it is the most nonpolar compound among these fractions because it came out of the silica gel column firstly. Compound 1 showed no activity against either *E. coli* or *L. innocua*. Compound 2 is the desired product PBC-FA, its MIC and MBC against *L. innocua* are both 7.3 ppm, showing strong biocidal activity against *L. innocua* but no activity to *E. coli*. Compound 3 is the imidazoline product which even has a higher *L. innocua* biocidal activity than PBC-FA, but it also has no activity against *E. coli*. Compound 4 is a mixture of lactone amide, lactone imidazoline and compound 2 and compound 3. Surprisingly, compound 4 is biocidal against both *E. coli* and *L. innocua*. Since compound 2 and compound 3 are not active against *E. coli*, it is believed that the lactone amide and lactone imidazoline contributed to the antimicrobial activity against *E. coli*. If compound 4 were incorporated in the crude PB C-FAA polymer film, it has a high chance to render the polymer to have good biocidal activity against *E. coli*.

thymol. The above composition, wherein R1 is carvacrol. The above composition, wherein R1 is not carvacrol.

The above composition, wherein R2 is ethylenediamine. The above composition, wherein R2 is not ethylenediamine. The above composition, wherein R2 is diethylenetriamine. The above composition, wherein R2 is not diethylenetriamine. The above composition, wherein R2 is triethylenetetramine. The above composition, wherein R2 is not triethylenetetramine. The above composition, wherein R2 is tetraethylenepentamine. The above composition, wherein R2 is not tetraethylenepentamine. The above composition, wherein R2 is hexamethylenediamine. The above composition, wherein R2 is not hexamethylenediamine.

The above composition, further containing (compound 1)

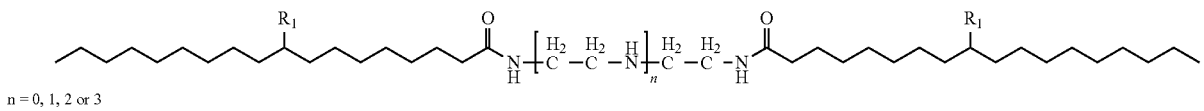

n = 0, 1, 2 or 3 where R1 is phenol, creosote, thymol, or carvacrol.

The above composition, further containing (compound 3)

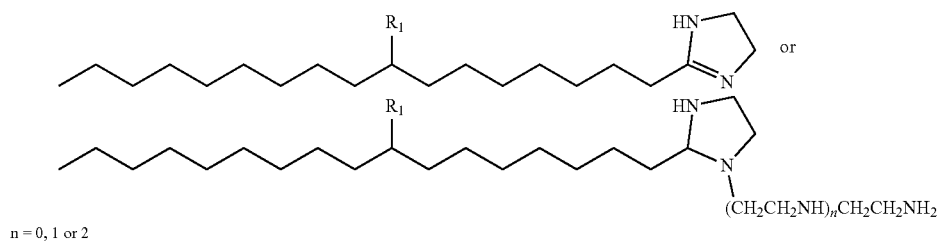

n = 0, 1 or 2 where R1 is phenol, creosote, thymol, or carvacrol.

The above composition, further containing at least one compound (the mixture) produced by a method comprising reacting PBC-FA methyl ester with at least one polyamine (e.g., ethylenediamine (EDA), diethylenetriamine (DETA), triethylenetetramine (TETA), tetraethylenepentamine (TEPA), hexamethylenediamine (HAD)).

The above composition, wherein at least one polyamine is ethylenediamine. The above composition, wherein at least one polyamine is not ethylenediamine. The above composition, wherein at least one polyamine is diethylenetriamine. The above composition, wherein at least one polyamine is not diethylenetriamine. The above composition, wherein at least one polyamine is triethylenetetramine. The above composition, wherein at least one polyamine is not triethylenetetramine. The above composition, wherein at least one polyamine is tetraethylenepentamine. The above composition, wherein at least one polyamine is not tetraethylenepentamine. The above composition, wherein at least one polyamine is hexamethylenediamine. The above composition, wherein at least one polyamine is not hexamethylenediamine.

The above composition, further containing at least one epoxy resin (e.g., bisphenol A type (based) epoxy resin such as diglycidyl ether of bisphenol A).

A method for killing microorganisms, said method comprising (or consisting essentially of or consisting of) con- All of the references cited herein, including U.S. Patents and U.S. Patent Application Publications, are incorporated by reference in their entirety. Also incorporated by reference in their entirety are the following references: U.S. Pat. Nos. 10,071,946; 10,144,694.

Thus, in view of the above, there is described (in part) the following:

A composition (compound 2) comprising (or consisting essentially of or consisting of) at least one compound of formula I

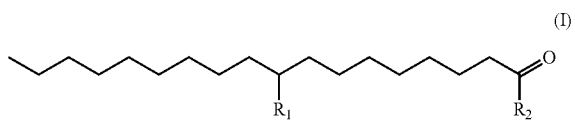

(I)

wherein R1 is a phenolic compound (e.g., simple phenol, creosote, thymol, or carvacrol), and wherein R2 is a polyamine (e.g., ethylenediamine (EDA), diethylenetriamine (DETA), triethylenetetramine (TETA), tetraethylenepentamine (TEPA), hexamethylenediamine (HDA)); and optionally a carrier.

The above composition, wherein R1 is phenol. The above composition, wherein R1 is not phenol. The above composition, wherein R1 is creosote. The above composition, wherein R1 is not creosote. The above composition, wherein R1 is thymol. The above composition, wherein R1 is not tacting said microorganisms with an effective microorganism killing amount of the above composition. The above method, wherein said microorganisms are selected from the group consisting of Gram-positive bacteria, Gram-negative bacteria, and mixtures thereof. The above method, where said microorganisms are Gram-positive bacteria. The above method, where said microorganisms are Gram-negative bacteria.

A composition comprising (or consisting essentially of or consisting of) at least one compound produced by a method comprising (or consisting essentially of or consisting of) reacting phenolic-branched chain fatty acid methyl ester methyl ester with at least one polyamine (e.g., ethylenediamine (EDA), diethylenetriamine (DETA), triethylenetetramine (TETA), tetraethylenepentamine (TEPA), hexamethylenediamine (HDA)); and optionally a carrier.

The above composition, wherein at least one polyamine is ethylenediamine. The above composition, wherein at least one polyamine is not ethylenediamine. The above composition, wherein at least one polyamine is diethylenetriamine. The above composition, wherein at least one polyamine is not diethylenetriamine. The above composition, wherein at least one polyamine is triethylenetetramine. The above composition, wherein at least one polyamine is not triethylenetetramine. The above composition, wherein at least one polyamine is tetraethylenepentamine. The above composition, wherein at least one polyamine is not tetraethylenepentamine. The above composition, wherein at least one polyamine is hexamethylenediamine. The above composition, wherein at least one polyamine is not hexamethylenediamine.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) which is not specifically disclosed herein. Thus, the specification includes disclosure by silence ("Negative Limitations In Patent Claims," AIPLA Quarterly Journal, Tom Brody, 41(1): 46-47 (2013): " . . . Written support for a negative limitation may also be argued through the absence of the excluded element in the specification, known as disclosure by silence . . . . Silence in the specification may be used to establish written description support for a negative limitation. As an example, in Ex parte Lin [No. 2009-0486, at 2, 6 (B.P.A.I. May 7, 2009)] the negative limitation was added by amendment . . . . In other words, the inventor argued an example that passively complied with the requirements of the negative limitation . . . was sufficient to provide support . . . . This case shows that written description support for a negative limitation can be found by one or more disclosures of an embodiment that obeys what is required by the negative limitation . . . ."

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

The Antimicrobial test results of epoxy films cured by different monomers

| Sample name | Listeria (L.) innocua ATCC 33090 (log CFU/ml) | Escherichia (E.) coli ATCC 700728 (log CFU/ml) |
|---|---|---|
| Blank | 6.59 ± 0.29 | 7.30 ± 0.39 |
| Purified PBC-FAA | <1 | 7.81 ± 0.20 |
| SAA | 6.33 ± 0.38 | 7.70 ± 0.37 |
| Crude PBC-FAA | <1 | <1 |
| EDA | 5.14 ± 0.92 | 7.29 ± 0.52 |

Bacteria strain used: E. coli ATCC 700728 (9 log CFU/mL), Listeria innocua ATCC 33090 (8 log CFU/ml)
The bacterial strains of E. coli ATCC 700728 and L. innocua ATCC 33090 were adjusted to approximately $10^3$ CFU/mL and $10^2$ CFU/mL, then add in vials with films to incubate at 37° C. and 100 RPM for 48 h and 24 h, respectively.
After incubation, the bacterial solution of E. coli ATCC 700728 was diluted $10^4$ times and the L. innocua ATCC 33090 was diluted $10^3$ times for plating.

TABLE 2

Formulas of the epoxy polymers.

| Entry | 1 mol polymer cured by | Curing agent needed in formula (g) | Epoxy resin needed in formula (g) |
|---|---|---|---|
| 1 | Creosote-BC-FAA (EDA) | 1.00 | 0.76 |
| 2 | Thymol-BC-FAA (EDA) | 1.00 | 0.72 |
| 3 | Carvacrol-BC-FAA (EDA) | 1.00 | 0.72 |
| 4 | Phenol-BC-FAA (HDA) | 1.00 | 0.72 |
| 5 | Phenol-BC-FAA (DETA) | 1.00 | 1.10 |
| 6 | Phenol-BC-FAA (TETA) | 1.00 | 1.35 |
| 7 | Phenol-BC-FAA (TEPA) | 1.00 | 1.55 |

TABLE 3

The comparison of epoxy polymers made from different phenolic BC-FAAs at two different temperatures

| Samples | Listeria (L.) innocua ATCC 33090 (log CFU/ml) | Escherichia (E.) coli ATCC 700728 (log CFU/ml) | Salmonella Typhimurium ATCC 53647 (log CFU/ml) |
|---|---|---|---|
| Blank control | 7 ± 0.01 | 7 ± 0 | 7 ± 0.03 |
| Phenol (97%) BC-FAA (EDA90° C.) | 4.46 ± 0.41 | 7.29 ± 0.26 | 7.02 ± 0.19 |
| Phenol (72%) BC-FAA (EDA90° C.) | 1 | 7.29 ± 0.13 | 7.11 ± 0.03 |
| Creosote (98%) BC-FAA (EDA90° C.) | 4.55 ± 0.47 | 7.55 ± 0.07 | 6.99 ± 0.03 |
| Thymol (86%) BC-FAA (EDA90° C.) | 7.01 ± 0.14 | 7.28 ± 0.15 | 7.05 ± 0.04 |
| Thymol (97%) BC-FAA (EDA90° C.) | 6.87 ± 0.2 | 7.25 ± 0.11 | 6.84 ± 0.17 |
| Carvacrol (83%) BC-FAA (EDA90° C.) | 6.65 ± 0.31 | 7.48 ± 0.28 | 6.66 ± 0.12 |
| Phenol (97%) BC-FAA (EDA160° C.) | 1 | 1 | 1 |

TABLE 3-continued

The comparison of epoxy polymers made from different phenolic BC-FAAs at two different temperatures

| Samples | Listeria (L.) innocua ATCC 33090 (log CFU/ml) | Escherichia (E.) coli ATCC 700728 (log CFU/ml) | Salmonella Typhimurium ATCC 53647 (log CFU/ml) |
| --- | --- | --- | --- |
| Phenol (72%) BC-FAA (EDA160° C.) | 1 | 1 | 1 |
| Creosote (98%) BC-FAA (EDA160° C.) | 1 | 1 | 1 |
| Thymol (97%) BC-FA (EDA210° C.) | — | 7.13 ± 0.5 | — |
| Thymol (7% phenol) BC-FAA (EDA160° C.) | — | 7.01 ± 0.04 | — |

TABLE 4

The comparison of epoxy polymers made from different polyamines at two different temperature

| Samples | Listeria (L.) innocua ATCC 33090 (log CFU/ml) | Escherichia (E.) coli ATCC 700728 (log CFU/ml) | Salmonella Typhimurium ATCC 53647 (log CFU/ml) |
| --- | --- | --- | --- |
| Blank control | 7 | 7 | 7 |
| Phenol (97%) BC-FAA (EDA160° C.) | 1 | 1 | 1 |
| Phenol (97%) BC-FAA (DETA210° C.) | 7.17 ± 0.06 | 6.86 ± 0.19 | 7.14 ± 0.06 |
| Phenol (97%) BC-FAA (TETA210° C.) | 7.22 ± 0.06 | 6.86 ± 0.29 | 7.09 ± 0.07 |
| Phenol (97%) BC-FAA (TEPA210° C.) | 7.21 ± 0.06 | 6.76 ± 0.1 | 6.93 ± 0.1 |
| Phenol (72%) BC-FAA (HDA160° C.) | 7 | 7 | — |

TABLE 5

The reusability test of Phenol 97% BCFAA (EDA, 160° C.) and Phenol 72% BCFAA (EDA, 160° C.) against E. coli.

| Reuse Time | Phenol 97% BCFAA (EDA, 160° C.) Replicate Number | | | Phenol 72% BCFAA (EDA, 160° C.) Replicate Number | | |
| --- | --- | --- | --- | --- | --- | --- |
|  | 1 | 2 | 3 | 1 | 2 | 3 |
| First | <1 | <1 | <1 | <1 | <1 | <1 |
| Second | <1 | <1 | <1 | <1 | <1 | <1 |
| Third | 2.79 ± 0 | <1 | <1 | 6.32 ± 0.05 | <1 | <1 |

TABLE 6

The MIC and MBC of the compounds in FIG. 5

| Compounds in FIG. 5 | Listeria (L.) innocua ATCC 33090 | | Escherichia (E.) coli ATCC 700728 | |
| --- | --- | --- | --- | --- |
|  | MIC | MBC | MIC | MBC |
| 1 | >232.7 | >232.7 | >232.7 | >232.7 |
| 2 | 7.3 | 7.3 | >232.7 | >232.7 |
| 3 | 3.6 | 3.6 | >232.7 | >232.7 |
| 4 | 3.6 | 3.6 | 29.1 | 29.1 |

We claim:

1. An antimicrobial epoxy polymer comprising a curing agent with structure:

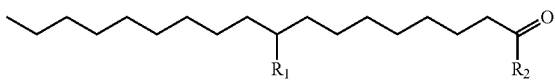

where $R_1$ is a phenolic group, and where $R_2$ is a polyamine group.

2. The epoxy polymer of claim 1 wherein $R_1$ is:

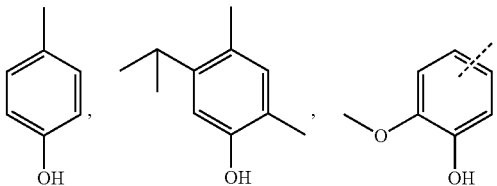

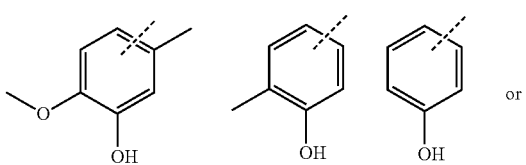

or

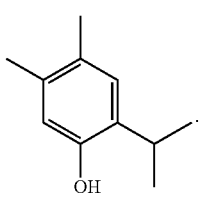

3. The epoxy polymer of claim 1 wherein the polyamine group is: ethylenediamine, diethylenetriamine, triethylenetetramine, tetraethylenepentamine or hexamethylenediamine.

4. A composition comprising at least one compound of formula I

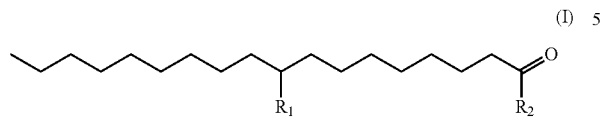
(I)

where R1 is a phenolic group, and where R2 is a polyamine group; and a carrier.

5. The composition according to claim 4, further comprising

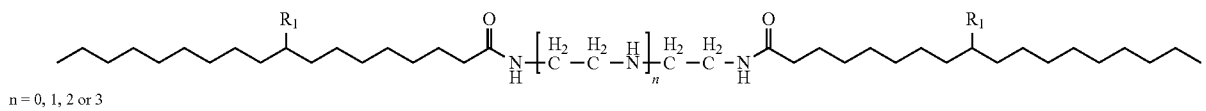

n = 0, 1, 2 or 3 where R1 is

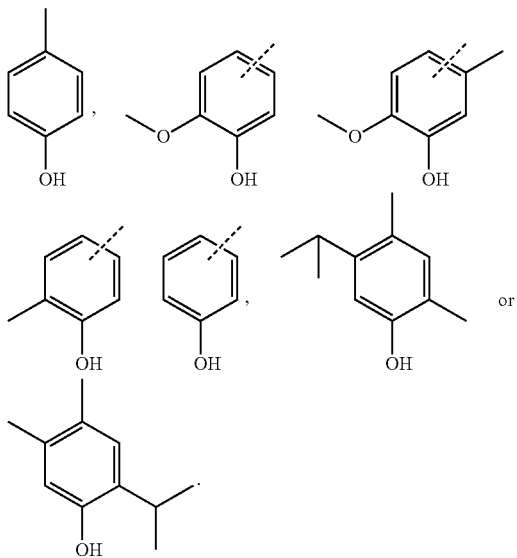

or

6. The composition according to claim 4, wherein the polyamine group is: ethylenediamine, diethylenetriamine, triethylenetetramine, tetraethylenepentamine or hexamethylenediamine.

7. A method for killing microorganisms, said method comprising contacting said microorganisms with an effective microorganism killing amount of the composition according to claim 1.

8. The method according to claim 7, wherein said microorganisms are selected for the group consisting of Gram-positive bacteria, Gram-negative bacteria, and mixtures thereof.

9. The method according to claim 7, where said microorganisms are Gram-positive bacteria.

10. The method according to claim 7, where said microorganisms are Gram-negative bacteria.

* * * * *